(12) United States Patent
Bhattacharya et al.

(10) Patent No.: US 7,173,152 B2
(45) Date of Patent: Feb. 6, 2007

(54) ONE-POT REDUCTIVE ACETAMIDATION OF ARYL NITRO COMPOUNDS

(75) Inventors: Apurba Bhattacharya, Corpus Christi, TX (US); Victor Suarez, Kingsville, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 11/208,474

(22) Filed: Aug. 19, 2005

(65) Prior Publication Data

US 2006/0052638 A1   Mar. 9, 2006

Related U.S. Application Data

(60) Provisional application No. 60/603,317, filed on Aug. 19, 2004.

(51) Int. Cl.
*C07C 233/05* (2006.01)

(52) U.S. Cl. .................................................. 564/223

(58) Field of Classification Search ................. 564/223
See application file for complete search history.

(56) References Cited

OTHER PUBLICATIONS

Nahmed et al, Tetrahedron Lett., 1991, vol. 32(37), abstract only.*

* cited by examiner

*Primary Examiner*—Shailendra Kumar
(74) *Attorney, Agent, or Firm*—Chalker Flores, LLP; Edwin S. Flores; Daniel J. Chalker

(57) ABSTRACT

The present invention provides a method for the reductive acetamidation of an aryl nitro compound by reacting a substituted acid with an aryl nitro compound and adding a catalytic amount of a base with the substituted acid and the aryl nitro compound to form an acetamidation aryl nitro compound. The acetamidation aryl nitro compound is then purified.

16 Claims, 1 Drawing Sheet

ONE-POT REDUCTIVE ACETAMIDATION OF ARYL NITRO COMPOUNDS

This application claims priority to the U.S. Provisional Application Ser. No. 60/603,317, filed Aug. 19, 2004, the contents of which are incorporated by reference herein in its entirety.

The U.S. Government may own certain rights to this invention under NIH Grant No. 1R25GM068940-01. Without limiting the scope of the invention, its background is described in connection with reductive acetamidation of aryl nitro compounds, as an example.

TECHNICAL FIELD OF THE INVENTION

The present invention relates general to chemical synthesis, and in particular, to one-pot reductive acetamidation of aryl nitro compounds by in situ catalytic re-generated thioacetate anion.

BACKGROUND OF THE INVENTION

Over the past few years, significant research has been directed toward the development of new technologies for environmentally benign processes (e.g., green chemistry), which are both economically and technologically feasible. One important area of green chemistry deals with solvent minimization.

Solvent minimization processes are those conducted in minimal amount of solvent or conducted in solvent-free environments. Solvent-free environments generally exhibit the high efficiency, while eliminating the costs of processing, handling and disposal of the solvent. Limited success has been achieved with solvent minimization processes employing aqueous systems, ionic liquids, immobilized solvents, dendrimers, amphiphilic star polymers or supercritical fluids. The major challenge encountered in solvent minimization processes is the lack of a common phase (e.g., the solvent medium) that brings the reactants into closer proximity.

Solvent minimization processes are especially desired in the manufacture of certain compounds used as active ingredients in pharmaceuticals. Examples of the solvent processes to synthesize N-acetyl-p-aminophenol (acetaminophen, sold under the trademark Tylenol®) are the Mallinckrodt Process, Celanese Process, Sterling Process and Monsanto Process, known to those with ordinary skill in the art.

For example, the Monsanto Process is described in U.S. Pat. Nos. 3,334,587 and 3,076,030, both of which are herein incorporated by reference, as well as the Sterling Process. The p-nitrophenol is reduced to p-aminophenol and then acetylated to render N-acetyl-p-aminophenol. Unfortunately, the processes of the prior art require the use of undesirable solvents.

In the Celanese Process, as described in U.S. Pat. No. 4,954,652, incorporated herein by reference, N-acetyl-para-aminophenol is prepared by subjecting 4-hydroxyacetophenone oxime to a Beckman rearrangement in the presence of a thionyl chloride catalyst and an alkyl alkanoate as the reaction solvent. Like the other processes of the prior art, the Celanese Process requires the use of an organic solvent.

Since acetaminophen is the most prescribed analgesic in the world because of its antipyretic activity, a solvent minimized process is desired. Some success has been achieved in co-pending U.S. patent application Ser. No. 10/666,543, entitled "Method of Producing Organic Compounds in Presence of Oxyethylene Ether Catalyst and in a Solvent Minimized Environment," which is assigned to a common assignee and incorporated herein by reference. A corollary publication is Bhattacharya, A.; Purohit, V.; Rinaldi, F. *Org. Proc. Res. Dev.* 2003, 7, 254, also incorporated herein by reference. In at least one embodiment, the application discloses a simple and highly efficient potassium thioacetate mediated one-pot conversion of aryl nitro compounds to aryacetamides. The reactions are conducted by employing potassium thioacetate (4 eq.) as a nucleophile in dipolar aprotic solvents such as DMF or in a solvent-free environment in presence of catalytic amounts of polyethylene glycol (PEG) type surfactants such as Triton-X. Further, crownether-like complementary nature of the various types of Triton-X and its differential solubilization tendencies for specific counterions has been demonstrated. Rebeck, J. *Angew. Chem. Int. Ed. Engl.* 1990, 29, 245. March, J. *Adv. Org. Chem.* 4$^{th}$ Ed. John Wiley, 82–93 and references cited therein.

Although the acetamidation proceeds well with useful level of conversion and efficiency in the above referenced patent application, its utility is limited by the use of large amount of relatively expensive potassium thioacetate. The process is also encumbered by undesirable amounts of salt-waste formation leading to complex isolation as well as higher disposal cost. Furthermore, use of stoichiometric amounts of the highly nucleophilic thioacetate anion is associated with unwanted nucleophilic displacement of halogen in the aromatic system.

Aryl amides have been demonstrated to be versatile and useful synthetic intermediate and are important structural elements of several drugs and candidates.[1] Traditional two-step syntheses of N-arylacetamides involving reduction of nitroarenes to N-arylamines followed by acylation to the corresponding N-arylacetamides employing activated carboxylic acids are well documented. Accordingly, a variety of methods for the reduction of nitro groups to amines using various metal catalysts, such as platinum oxide, rhodium-platinum oxide, palladium, Raney Ni, copper, ruthenium sulfide, zinc and iron as well as samarium, indium, or Bakers' yeast have been developed. See, e.g. Nishimura, S. *Bull. Chem. Soc. Jpn.* 1961, 34, 32. Adams, R.; Cohen, F. L. *Org. Syn. Coll.* 1932, 1, 240. Mendennhall, G. D.; Smith, P. A. S. *Org. Syn. Coll.* 1973, 5, 829. Adkins, H.; R. Connar. *J. Am. Chem. Soc.* 1931, 53, 1091. Davies, R. R.; Hodgson, H. H. J. Chem. Soc. 1943, 281. Broadbent, H. S.; Slaugh, L. H.; Jarvis, N. L. *J. Am. Chem. Soc.* 1954, 76, 1519. Tsukinoki, T.; Tsuzuki, H. *Green. Chem.* 2001, 3, 37–38. Hodgson, H. H.; Whitehurst, J. S. *J. Am. Chem. Soc.* 1945, 202. Wang, L.; Zhou, L.; Zhang, *Synlett*. 1999, 1065. Pitts, M. R.; Harrison, J. R.; Moody, C. J. *J. Chem. Soc., Perkin Trans.* 2001. 1. 955. Blackie, J. A.; Turner, N.J.; Wells, A. S. *Tetrahedron Lett.* 1997, 38, 3043, these references being incorporated by reference.

SUMMARY OF THE INVENTION

The present inventors recognized a need for a more commercially attractive process for acetamidation of organic compounds, including nitro compounds, and even more advantageously one that is solvent-minimized.

The invention provides an efficient salt-reduced, environmentally friendly, one-pot acetamidation of aryl nitro compounds under essentially non-nucleophilic conditions. The reaction can be performed without solvent in presence of catalytic amounts of surfactant and base. The process provides a facile and cost-effective surfactant mediated one-pot reductive acetamidation of aryl nitro derivatives using inexpensive thioacetic acid in conjunction with catalytic amounts of base such as potassium carbonate through in situ catalytic generation of thioacetate anion as the nucleophile. The acetamidation chemistry converts p-nitrophenol in a single step to p-hydroxyacetamide (acetaminophen or Tylenol®) in approximately 90% conversion. The fact that the reactions proceed to high conversions, selectivity and vessel efficiency renders the process practical and economically attractive and demonstrates yet another facet of the utility of the surfactant mediated solvent free technology in organic synthesis. This invention can also have applicability to the synthesis of heterocycles starting from suitably substituted aryl 2-nitro derivatives.

A direct one-step conversion of nitro to acetamides without the intermediacy of the amine and the obligatory activation of carboxylic acid would be highly desirable. However, existing methods for effecting such transformation are few; suffer from limited utility and also unwanted byproduct formation such as N,O-diacetylated derivative. Kim, B. H.; Han, R.; Piao, F.; Jun, Y. M. Baik, W.; Lee, B. M. Tetrahedron Lett 2003, 44, 77, also incorporated herein by reference. A limited solution to the unwanted derivative appeared in a report describing an efficient reduction of aromatic nitro compounds to the corresponding aryl amines employing sodium trimethylsilanethiolate (NaSTMS). The proposed reduction mechanism involves a nucleophilic attack by TMS-S$^{(-)}$ on the —NO$_2$ group accompanied by an intramolecular TMS shift from sulfur to oxygen and eventual extrusion of sulfur. See e.g., Hwu,k J. R.; Wong, F. F.; Shiao, M-J. J. Org. Chem. 1992, 57, 5254. Shiao, J—J.; Long-Li, L.; Wei-Shan, K.; Lin, P-Y.; Hwu, *J. R. J. Org. Chem.* 1993, 58, 4742, incorporated herein by reference. However, the efficient acetamidation of nitro compounds eluded those in this field.

In accordance with the present invention, a method and composition are provided that include a one-pot method for the reductive acetamidation of an aryl nitro compound by reacting a substituted acid with an aryl nitro compound and adding a catalytic amount of a base with the substituted acid and the aryl nitro compound to form an acetamidation aryl nitro compound. The acetamidation aryl nitro compound is then purified.

For example, a method is provided that include a one step method of converting p-nitrophenol to p-hydroxyacetamide by adding a thioacetic acid to a p-nitrophenol and adding a catalytic amount of a carbonate to the thioacetic acid and the p-nitrophenol, whereby the p-nitrophenol is converted to a p-hydroxyacetamide. The p-hydroxyacetamide is then purified.

In addition the present invention, includes a method for the solvent-free nitroamidation of an aryl nitro compound by reacting an acid and an aryl nitro compound and adding a catalytic amount of a base with the acid and the aryl nitro compound to form a substituted aryl nitro compound. The substituted aryl nitro compound is then purified.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
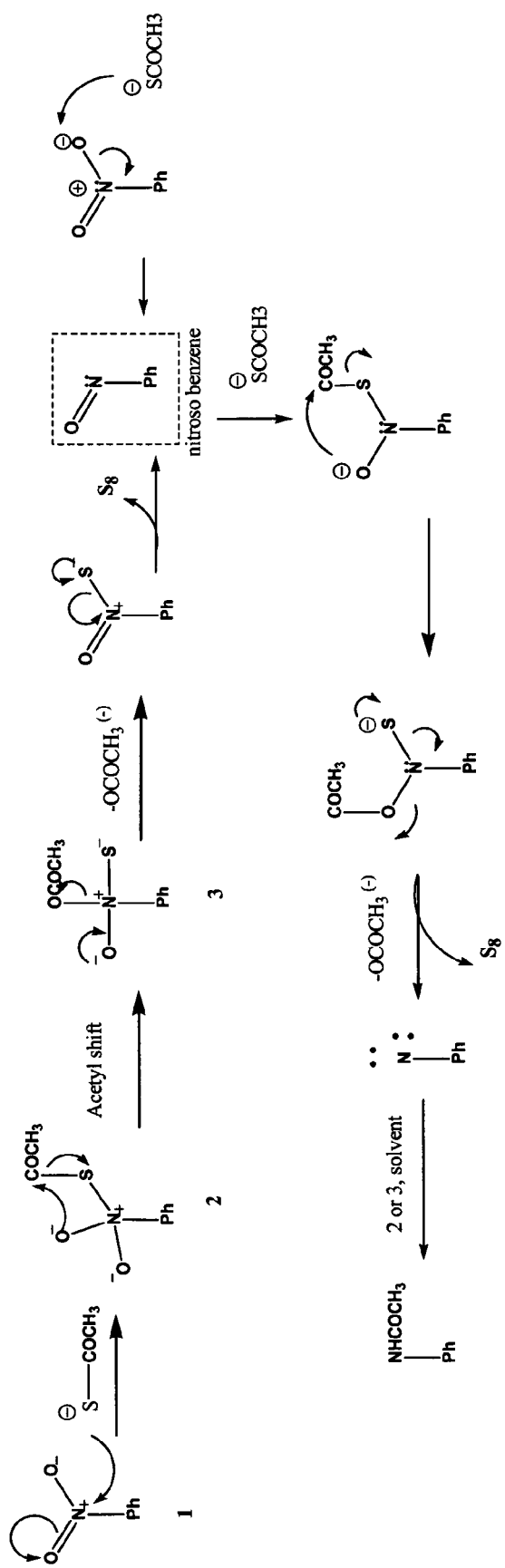
FIG. 1 is a schematic that illustrates the reduction process of the present invention.

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

As used herein, the term "alkoxy" denotes —OR—, wherein R is alkyl. The term "alkylcarbonyl" denote an alkyl group substituted with a C(O) group, for example, CH$_3$ C(O)—, CH$_3$ CH$_2$ C(O)—, etc. The term "alkylcarboxyl" denote an alkyl group as defined above substituted with a C(O)O group, for example, CH$_3$ C(O)O—, CH$_3$ CH$_2$ C(O)O—, etc.

As used herein, the term "amido" denotes an amide linkage: —C(O)NHR (wherein R is hydrogen or alkyl). The term "amino" denotes an amine linkage: —NR—, wherein R is hydrogen or alkyl.

As used herein, the term "aryl" denotes a chain of carbon atoms which form at least one ring having between about 4–14 carbon atoms, such as phenyl, naphthyl, and the like, and which may be substituted with one or more functional groups, which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like. For example, the aryl may be a monocyclic or bicyclic structure having 4 to 14, preferably 5 to 6, ring atoms and the ring members can be further substituted with alkyl groups, such as methyl, ethyl, etc. Furthermore, the aryl may be substituted with one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

The present invention includes a one-pot method for the reductive acetamidation of an aryl nitro compound by reacting a substituted acid and an aryl nitro compound and adding a catalytic amount of a base with the substituted acid and the aryl nitro compound to form an acetamidation aryl nitro compound. The acetamidation aryl nitro compound can then be purified. The purification can take the form of one or more distillative removals or other purification methods known to the skilled artisan, e.g., extraction, column chromatography, HPLC, etc.

The substituted acid may be a variety of acids commonly used in organic synthesis including thioacetic acid; however, the skilled artisan will recognize other acids may also be used, e.g., thioproponic acid, thiobutyric acid, thiovinylacetic acid or mixtures thereof.

The present invention provides the acetamidation of an aryl nitro compound. The aryl nitro compound may include both monocyclic rings and bicyclic rings having 4 to 14, preferably 5 to 6 ring atoms. Furthermore, the ring members can be further substituted with alkyl groups, such as methyl, ethyl, etc. Additionally, the aryl may be substituted with one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof. The substitutions to the aryl nitro compound may be at the ortho position, para position, meta position or combinations thereof, e.g., a p-nitro aryl, an o-nitro aryl, m-nitro aryl or a combination thereof.

In some embodiments, the catalytic amount of the base added is between about 1 and 10 mole percent and in some instances about 5 mole percent. Generally, the base is a carbonate and more specifically potassium carbonate; however, other counter ions may be used. Alternatively, the base may be a sulphate, a borate, a nitrate or combinations thereof.

For example, the present invention provides a one-step method of converting p-nitrophenol to p-hydroxyacetamide by adding a thioacetic acid to a p-nitrophenol and adding a catalytic amount of a carbonate to the thioacetic acid and the p-nitrophenol, whereby the p-nitrophenol is converted to a p-hydroxyacetamide. The p-hydroxyacetamide is then purified. The purification can take the form of one or more distillative removals or other purification methods known to the skilled artisan, e.g., extraction, column chromatography, HPLC, etc.

The present invention also provides the p-hydroxyacetamide made by adding a thioacetic acid to a p-nitrophenol and adding a catalytic amount of a carbonate to the thioacetic acid and the p-nitrophenol, whereby the p-nitrophenol is converted to a p-hydroxyacetamide. The p-hydroxyacetamide is then purified. The purification can take the form of one or more distillative removals or other purification methods known to the skilled artisan.

The present invention provides a method for the solvent-free nitroamidation of an aryl nitro compound by reacting an acid with an aryl nitro compound and adding a catalytic amount of a base with the acid and the aryl nitro compound to form a substituted aryl nitro compound. The substituted aryl nitro compound can then be purified. The purification can take the form of one or more distillative removals or other purification methods known to the skilled artisan.

Generally, the substituted acid is a thioacetic acid; however, the skilled artisan will recognize other acids commonly used in organic synthesis may also be used, e.g., thioproponic acid, thiobutyric acid, thiovinylacetic acid or mixtures thereof. Similarly, one base used with the present invention is a carbonate; however, other bases commonly used in organic synthesis may also be used (e.g., a carbonate, a sulphate, a borate, a nitrate, or combinations thereof) and the catalytic amount of the base may vary between about 1 and 10 mole percent.

The present invention provides the acetamidation of an aryl nitro compound having one or more rings with 4 to 14 ring atoms. Furthermore, the aryl may have one or more substitutions at the ortho position, para position, meta position or combinations thereof. The substitutions include one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

The present invention also provides the nitroamidated aryl nitro compound made by reacting an acid with an aryl nitro compound and adding a catalytic amount of a base with the acid and the aryl nitro compound to form a substituted aryl nitro compound. The substituted aryl nitro compound can then be purified. The purification can take the form of one or more distillative removals or other purification methods known to the skilled artisan.

FIG. 1 is a schematic that illustrates the reduction mechanism of the present invention. Initially, the mechanism for the reductive acetamidation involves a sequential nucleophilic attack of the thioacetate anion on the nitro function producing the acyl intermediate [2] followed by an energetically favorable intramolecular acetyl shift from S to oxygen producing the second acyl intermediate [3]; both the acyl intermediates [2] and [3] are believed to act as in-situ acetyl donor equivalents in a bimolecular fashion leading directly to the desired acetanilide after extrusion of elemental sulfur and acetate anion, as shown in FIG. 1.

Thioacetic acid is a stronger acid (pKa=3.33) than acetic acid (pKa=4.76). The acetate anion generated in the scheme should deprotonate thioacetic acid, regenerating the thioacetate anion and thereby rendering the process catalytic with respect to thioacetate anion. Thus, the process could be carried out in thioacetic acid itself in presence of catalytic amount of a base such as potassium carbonate.

The invention provides a simple, efficient one-pot acetmidation of aryl nitro compounds using a unique acid base system consisting of thioacetic acid in conjunction with catalytic amounts of potassium carbonate under essentially salt-free conditions.

In at least one embodiment, the solvent-free nitroamidation protocol involves treating a mixture of the aryl nitro compound (1 eq) with thioacetic acid (4–8 eq) and potassium carbonate (e.g., about 5 mole %) at about 130° C. for about 3 hours giving rise to the corresponding arylacetamide in greater that about 80% conversion (e.g., HPLC and GC) and selectivity. Since the reaction is conducted in absence of a large amount of a strong sulfur nucleophile, it obviates the shortcomings associated with the undesired nucleophilic displacement of aryl halides.

Thus, aryl bromo nitro derivatives can be efficiently converted to the corresponding bromoaetamides without any displacement of the bromides (entry 5, 6 and 7). When potassium thioacetate was employed as a nucleophile under otherwise identical conditions, nucleophilic displacement of the aryl halide with thioacetate was observed. The process is essentially salt-free. The reaction is performed neat; the product is directly obtained by distillative removal of thioacetic acid. No exhaustive work-up to remove the large amounts of salt was necessary thus leading to significant process simplicity. These conditions were successfully applied to prepare various arylacetamides from a representative group of aryl nitro compounds in consistently high yield, as shown in Table 1.

TABLE 1
Acetamidation of Arynitro compounds given the general reaction:
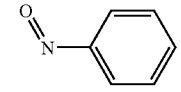
| | Starting Material | HPLC Conversion | RXN Time |
|---|---|---|---|
| 1 | 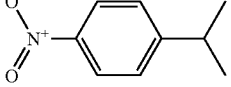 | 85% | 3 Hrs |
| 2 | 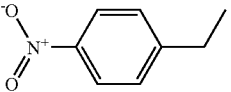 | 80% | 24 Hrs |
| 3 | 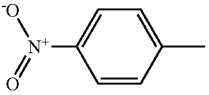 | 78% | 24 Hrs |
| 4 | 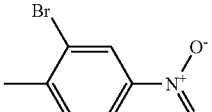 | 75% | 24 Hrs |
| 5 | 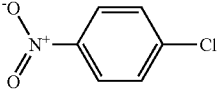 | 85% | 10 Hrs |
| 6 | 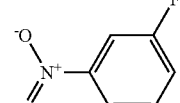 | >90% | 4 Hrs |
| 7 | 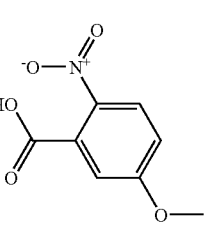 | 80% | 12 Hrs |
| 8 |  | 75% | 24 Hrs |
| 9 | 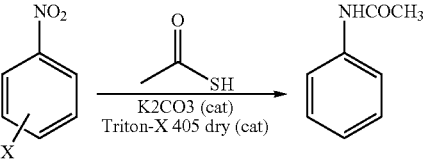 | >90% | 14 Hrs |
TABLE 1-continued
Acetamidation of Arynitro compounds given the general reaction:
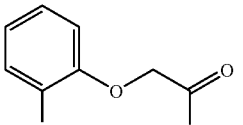
| | Starting Material | HPLC Conversion | RXN Time |
|---|---|---|---|
| 10 | 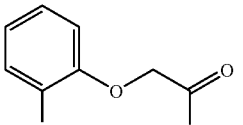 | 85% | 24 Hrs |
| 11 | 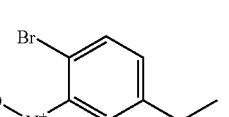 | 80% | 24 Hrs |
| 12 | 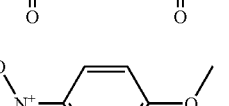 | 80% | 24 Hrs |
| 13 | 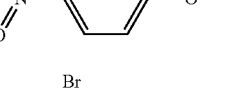 | 85% | 24 Hrs |
| 14 | 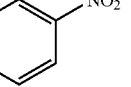 | 85% | 24 Hrs |
| 15 | 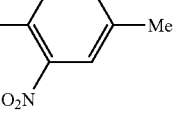 | 80% | 24 Hrs |
| 16 | 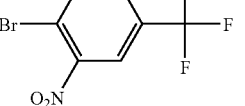 | 80% | 24 Hrs |
| 17 | 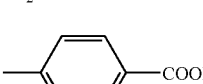 | 70% | 16 Hrs |
| 18 | 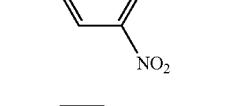 | 80% | 24 Hrs |

TABLE 1-continued

Acetamidation of Arynitro compounds given the general reaction:

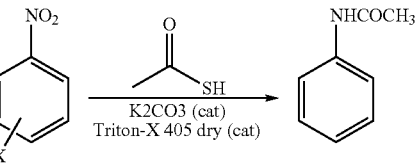

| | Starting Material | HPLC Conversion | RXN Time |
|---|---|---|---|
| 19 | H3COOC—[O2N-phenyl] | 75% | 24 Hrs |

The one-step acetamidation method off the present invention was used to convert p-nitrophenol in a single step to p-hydroxyacetamide (acetaminophen or Tylenol®) in greater than about a 90% conversion.

In one example, under nitrogen gas, a stirred mixture of 4-Chloro-1-nitrobenzene (e.g., about 1 g, 6.35 mmol), thioacetic acid (e.g., about 1.93 g, 25.39 mmol), $K_2CO_3$ (e.g., about 0.050 g, 0.36 mmol), and dry Triton-X 405 (e.g., about 0.010 g) were heated at about 150° C. The progress of the reaction was monitored by HPLC and GC. After four hours the reaction was cooled to room temperature, and acetone (e.g., about 8 mL) was added and filtered through a sintered glass funnel. Evaporation of the acetone produced about 0.975 g of N-(4-Chloro-phenyl)-acetamide (e.g., about 91%).

The scheme illustrated in FIG. 1 represents the process that provides the reductive amidation of $NO_2$ in the present invnetion, as attested by the results. Sequential nucleophilic attack of the thioacetate anion producing the acyl intermediate [A] appears to be followed by an energetically favorable intramolecular acetyl shift from S to oxygen producing the second acyl intermediate [B]; both the acyl intermediates A and B potentially act as in-situ acetyl donor equivalents in a bimolecular fashion and lead directly to the desired acetanilide after sulfur extrusion. This data uses the average bond energy of C—S is about 65 k cal/mole, C—C is about 83 k cal/mole and C—Si is about 83 k cal/mole, where the data was obtained from Michigan State University.

Preliminary results have confirmed various steps in the process. For example, preliminary results indicated the formation of $S_8$ (e.g., fingerprint GCMS) in the reaction as depicted in the FIG. 1. Subjecting nitrosobenzene (a proposed intermediate in the reaction) with potassium thioacetate (3 eq) under otherwise identical conditions smoothly produced the acetanilide in greater that about 95% conversion providing indirect support for the hypothesis. No reaction was observed when potassium thioacetate was replaced with thioacetic acid under otherwise identical conditions. Particularly remarkable is the fact that 1-hydroxy-2-nitronaphthalene when subjected to the acetamidation conditions (e.g., $CH_3COSK$, 4 eq, about 130° C.) smoothly produced the corresponding oxazole derivative via cyclization of the —OH and the amide group.

An alternate mechanism involves S—S bond formation thereby delivering two electrons in the form of a hydride (H—) which takes part in the reduction of the —NO$_2$ functionality. The S—S bond formation has precedence in peptide chemistry of cystein. The resulting dithiane can also act as an effective acylating agent producing the acylated amine.

The conversion of nitrobenzene to acetamide, as a representative example, employing potassium or sodium thioacetate in solvents such as MTBE, toluene or ethyl acetate, phase transfer conditions or high temperature (e.g., about 130° C. sealed tube) produced the desired product in trace (less than about 10%) amounts. DMF was used as a solvent to increase nucleophilicity as well as solubility of the reagent dramatically improved the acetamidation reaction rate, leading to faster cleaner conversion. Thus, optimal conditions to effect the nitroamidation reactions involved treating a mixture of the aryl nitro compound (1 eq) with potassium thioacetate (4 eq.) in DMF (e.g., about 2 mL/g) at about 130° C. for about 3 hours giving rise to the corresponding arylacetamide in greater than about 95% conversion (HPLC and GC) and selectivity. These conditions were successfully applied to prepare various arylacetamides from a representative group of aryl nitro compounds in good to excellent yields after aqueous work-up. The products were identified by finger print GCMS and NMR.

Generally, the procedure is as follows: under nitrogen gas, a stirred mixture of potassium thioacetate (e.g., about 3.71 g, 32.5 mmol), nitrobenzene (e.g., about 1 g, 8.1 mmol) and DMF (e.g., about 2.0 ml) is heated at about 130° C. After two hours, the reaction mixture is cooled to room temperature, brine (e.g., about 2 ml) is added and the resulting mixture is extracted with tert-butyl methyl ether (e.g., about 2×15 ml). The combined organic layer is washed with brine (e.g., about 2×4 ml) to remove residual DMF and filtered through a pad of charcoal and Celite to remove any residual sulfur. Evaporation of the solvent produced about 0.9 g of acetanilide (about 83%).

Synthesis of Acetaminophen. The one-step acetamidation technology was successfully used to convert p-nitrophenol in a single step to p-hydroxyacetamide (acetaminophen or Tylenol®) in greater than about 95% conversion. Interestingly, p-nitroanisole when subjected to four equivalents of potassium thioacetate in DMF under otherwise identical conditions was also converted to acetaminophen as a result of concomitant nucleophilic cleavage of the methoxy group followed by acetamidation of the —NO$_2$; p-nitrophenol was produced as an intermediate in this process as evidenced by HPLC and GCMS analysis and p-nitrophenol was the major product when one equivalent of potassium thioacetate was used. Such thioacetate anion mediated nucleophilic cleavage constitutes a mild aryl alky ether cleavage under essentially neutral conditions. For example, the U.S. patent application Ser. No. 10/666,543 describes an efficient solvent minimized synthesis of nitroalcohols, using a novel dual catalytic system consisting of a mineral base such as KOH and polyethylene glycol (PEG) type Triton-X surfactant under homogeneous conditions.

Surfactant mediated solvent-free protocols were also successfully extended to the conversion of aryl nitro compounds to aryl acetamides. Thus, solvent-free acetamidation reactions involved treating a mixture of the aryl nitro compound (1 eq) with potassium thioacetate (4 eq.) in presence of dry Triton-X 405 (cat) at about 130° C. for about 3 hours producing the corresponding arylacetamide in greater than about 95% conversion (HPLC and GC) and selectivity. Representative results for acetamidation of aryl nitro compounds area summarized in Table 2.

TABLE 2

Thioacetate Mediated Acetamidation of Arylnitro Compounds:

$$\text{Ar}-\text{NO}_2 \xrightarrow[\text{Triton-X 405 (cat.), no solvent 130° C.}]{\text{KSCOCH}_3, \text{DMF, 130° C. or}} \text{Ar}-\text{NHCOCH}_3$$
1 → 2

| Entry | 1 | Time (h) | % Conversion[a] (% Yield) DMF | Solvent Free |
|---|---|---|---|---|
| 1 | C6H5–NO2 | 2 | 97(83) | 96(78) |
| 2 | C6H5–NO | 1 | 98(85) | 95(75) |
| 3 | 4-methyl-C6H4–NO2 | 2 | 94(85) | 95(77) |
| 4 | 3-methyl-C6H4–NO2 | 2 | 94(86) | 94(73) |
| 5 | 3,4-dimethyl-C6H3–NO2 | 2 | 95(88) | 95(78) |
| 6 | 4-hydroxy-C6H4–NO2 | 1 | 90(60) | 90(55) |
| 7 | 3-hydroxy-C6H4–NO2 | 1 | 90(62) | 88(58) |
| 8 | 2-hydroxy-C6H4–NO2 | 1 | 90(65) | 85(60) |
| 9 | 4-ethyl-C6H4–NO2 | 2 | 95(85) | 94(76) |
| 10 | 4-isopropyl-C6H4–NO2 | 2 | 95(88) | 93(79) |
| 11 | 4-acetyl-C6H4–NO2 | 1 | 80(65) | 70(60) |
| 12 | 3-chloro-4-methyl-C6H3–NO2 | 2 | 92(85) | 88(75) |
| 13 | 3-bromo-4-methyl-C6H3–NO2 | 2 | 95(85) | 90(78) |
| 14 | 2-nitrobiphenyl | 3 | 85(75) | 75(68) |
| 15 | 1-nitronaphthalene | 3 | 90(87) | 88(75) |
| 16 | 2-nitrofluorene | 2 | 80(75) | 77(64) |
| 17 | 2-methyl-1-nitronaphthalene | 3 | 98(87) | 95(78) |

TABLE 2-continued

Thioacetate Mediated Acetamidation of Arylnitro Compounds:

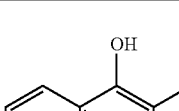

| Entry | 1 | Time (h) | % Conversion[a] (% Yield) | |
|---|---|---|---|---|
| | | | DMF | Solvent Free |
| 18 | 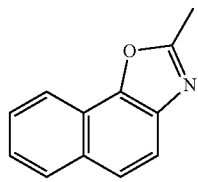 | 3 | 95(70)[b] | 93(65)[b] |

[a]Conversion based on GC and HPLC.

[b]Heterocyclic product was obtained

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Zhang, Z; Yin, A; Kadow, J. F.; Meanwell, N. A.; Wang, T. J. *J. Org. Chem*, 2004, 69. 1360.

"Lidocaine" in *Merck Index*, 12th Ed., S. Budavari ed., Merck & Co., Inc., 1996, 5505, p 936.

Ballini, R; Bosica, G; Fiorini, D. *Tetrahedron*. 1998, 59, 1143.

Katritzky, A. R.; He, H—Y.; Suzuki, K. *J. Org. Chem*, 2000, 65, 8210.

What is claimed is:

1. A one-pot method for the reductive acetamidation of an aryl nitro compound comprising the steps of:
   reacting a substituted acid, selected from the group consisting of thioacetic acid, thioproponic acid, thiobutyric acid, thiovinylacetic acid or mixtures thereof, with an aryl nitro compound;
   adding a catalytic amount of a base with the substituted acid and the aryl nitro compound to form an acetamidation aryl nitro compound; and
   purifying the acetamidation aryl nitro compound.

2. The method of claim 1, wherein the base comprises a carbonate, a sulphate, a borate, a nitrate or combinations thereof.

3. The method of claim 1, wherein the aryl nitro compound comprises a p-nitro aryl, an o-nitro aryl, m-nitro aryl or a combination thereof.

4. The method of claim 1, wherein the catalytic amount of the base comprises between about 1 and 10 mole percent.

5. The method of claim 1, wherein the step of purifying comprises one or more distillative removals.

6. The method of claim 1, further comprising DMF, MTBE, toluene, ethyl acetate or mixtures thereof.

7. A one step method of converting p-nitrophenol to p-hydroxyacetamide comprising the steps of:
   adding a thioacetic acid to a p-nitrophenol;
   adding a catalytic amount of a carbonate to the thioacetic acid and the p-nitrophenol, whereby the p-nitrophenol is converted to a p-hydroxyacetamide; and
   purifying the p-hydroxyacetamide.

8. The method of claim 7, wherein the step of purifying comprises one or more distillative removals, extraction or combinations thereof.

9. The method of claim 7, wherein the catalytic amount of the carbonate comprises between about 1 and 10 mole percent.

10. The method of claim 7, further comprising DMF, MTBE, toluene, ethyl acetate or mixtures thereof.

11. A method for the solvent-free nitroamidation of an aryl nitro compound comprising the steps of:
   reacting an acid, selected from the group consisting of thioacetic acid, thioproponic acid, thiobutyric acid, thiovinylacetic acid or mixtures thereof, with a aryl nitro compound;
   adding a catalytic amount of a base with the acid and the aryl nitro compound to form a substituted aryl nitro compound; and
   purifying the substituted aryl nitro compound.

12. The method of claim 11, wherein the catalytic amount of the base comprises between about 1 and 10 mole percent.

13. The method of claim 11, wherein the step of purifying comprises one or more distillative removals.

14. The method of claim 11, wherein the base comprises a carbonate, a sulphate, a borate, a nitrate, or combinations thereof.

15. The method of claim 11, wherein the aryl nitro compound comprises a p-nitro aryl compound, an o-nitro aryl compound, m-nitro aryl compound or a combination thereof.

16. The method of claim 11, further comprising DMF, MTBE, toluene, ethyl acetate or mixtures thereof.

* * * * *